United States Patent [19]

Turkel et al.

[11] Patent Number: 5,685,852
[45] Date of Patent: Nov. 11, 1997

[54] NEEDLE ASSEMBLY AND METHODS USEFUL FOR EPIDURAL ANESTHESIA

[75] Inventors: David Turkel, Miami; Frank A. Scarfone, Boca Raton, both of Fla.

[73] Assignee: Symbiosis Corporation, Miami, Fla.

[21] Appl. No.: 223,454

[22] Filed: Apr. 5, 1994

Related U.S. Application Data

[63] Continuation-in-part of Ser. No. 949,736, Sep. 23, 1992, Pat. No. 5,300,046, and Ser. No. 860,447, Mar. 30, 1992, Pat. No. 5,334,159.

[51] Int. Cl.$^6$ .................................................. A61M 5/178
[52] U.S. Cl. ........................... 604/159; 604/239; 604/264; 604/272; 604/51
[58] Field of Search ........................... 604/27, 28, 157, 604/158, 164, 170, 239, 272–274, 159, 167, 169, 51, 264; 128/753–755

[56] References Cited

U.S. PATENT DOCUMENTS

| | | | |
|---|---|---|---|
| 1,087,845 | 2/1914 | Stevens . | |
| 1,527,291 | 2/1925 | Zorraquin | 604/158 |
| 2,623,521 | 12/1952 | Shaw | 128/221 |
| 2,630,803 | 3/1953 | Baran | 128/221 |
| 2,922,420 | 1/1960 | Cheng | 604/158 |
| 4,808,168 | 2/1989 | Warring | 604/158 |
| 4,842,585 | 6/1989 | Witt | 604/274 |
| 4,869,717 | 9/1989 | Adair | 604/51 |
| 5,098,388 | 3/1992 | Kulkashi | 604/158 |
| 5,100,390 | 3/1992 | Lubeck et al. | 604/158 |
| 5,104,381 | 4/1992 | Gresl | 604/164 |
| 5,106,376 | 4/1992 | Mononen et al. | 604/158 |
| 5,139,485 | 8/1992 | Smith | 604/158 |
| 5,226,426 | 7/1993 | Yoon | 128/753 |
| 5,256,148 | 10/1993 | Smith | 604/158 |
| 5,322,512 | 6/1994 | Mohiuddin | 604/160 |
| 5,330,444 | 7/1994 | Webler et al. | 604/265 |
| 5,330,488 | 7/1994 | Goldrath | 604/170 |
| 5,374,252 | 12/1994 | Banks et al. | 604/158 |

*Primary Examiner*—Mark Bockelman
*Assistant Examiner*—Chalin Smith
*Attorney, Agent, or Firm*—David P. Gordon

[57] ABSTRACT

The needle assembly of the present invention includes a hollow cannula having a sharp distal end, a hollow stylet having a blunt distal end with a radial opening and an interior deflection surface near the radial opening, and a mechanism for biasing the stylet in a first position where the blunt distal end of the stylet extends beyond the sharp distal end of the cannula. Preferably, the hollow cannula hub has a proximal end which is coupled, e.g., via insert molding, to a hollow cannula hub. Likewise, the stylet preferably includes a proximal end which is coupled, e.g., via insert molding, to a hollow stylet hub which is longitudinally movable within the hollow cannula hub. The mechanism for biasing typically comprises a spring inside the cannula hub which biases the stylet hub to the first position where the blunt distal end of the stylet extends beyond the sharp distal end of the cannula. The stylet is movable against the spring to a second position where the sharp distal end of the cannula extends beyond the blunt distal end of the stylet. A first indicator is provided on the cannula hub showing the position of the stylet relative to the cannula and a cannular orientation indictor on the cannula shows the direction of the radial opening.

17 Claims, 4 Drawing Sheets

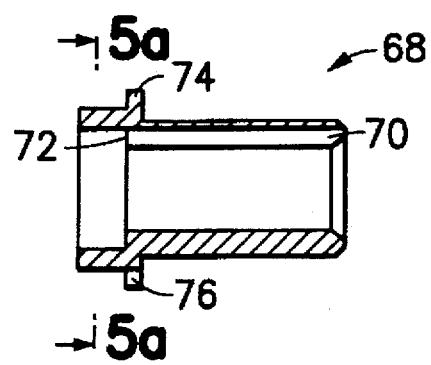
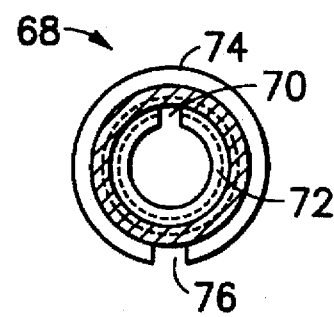
FIG. 5  FIG. 5a
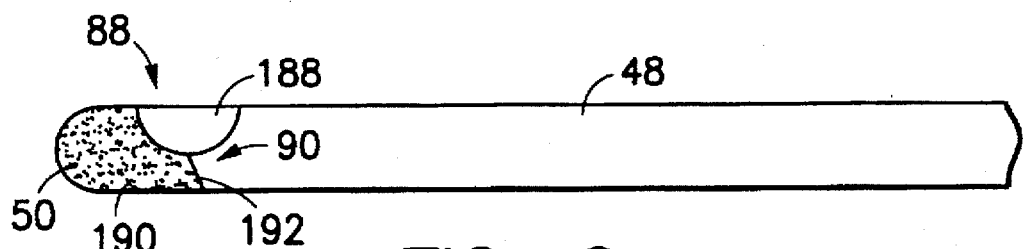
FIG. 6
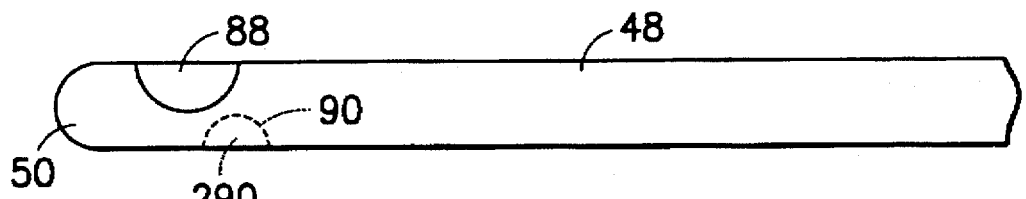
FIG. 7
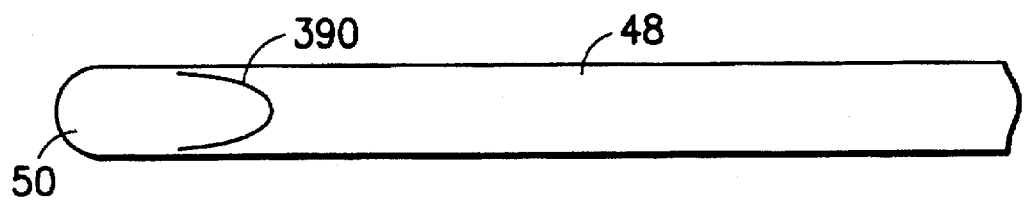
FIG. 8
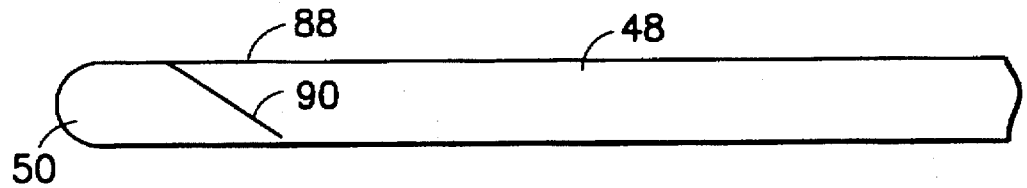
FIG. 8a

NEEDLE ASSEMBLY AND METHODS USEFUL FOR EPIDURAL ANESTHESIA

This is a continuation-in-part of co-owned U.S. Ser. Nos. 07/949,736 filed on Sep. 23, 1992, now U.S. Pat. No. 5,300,046 and 07/860,447 filed Mar. 30, 1992, now U.S. Pat. No. 5,334,159.

BACKGROUND OF THE INVENTION

1. Field of the Invention

The present invention relates generally to medical needle assemblies for use in locating and directing catheters. The present invention more particularly relates to improvements in needle assemblies utilizing blunt stylets which are useful for introducing catheters into narrow spaces which are angled relative to the insertion direction. The needle assembly and methods of the invention have particular application to epidural anesthesia, although they are not limited thereto.

2. State of the Art

Epidural anesthesia has gained popularity over the years as being an effective manner of blocking pain without requiring entry to the dura mater of the spinal cord (i.e., a spinal anesthesia). In fact, epidural anesthesia is often the anesthesia of choice in child birth. The preferred surgical procedure for epidural anesthesia starts with the utilization of a 17- or 18-gauge Touhy needle in the lumbar region in order to puncture the skin, and to traverse at least the supraspinous ligament. The Touhy needle is basically a hollow needle having an angled distal tip which is slightly curved (i.e., a Huber point) and a proximal luer fitting, and a solid stylet which sits inside and substantially fills the hollow needle. Once the skin and supraspinous ligament have been traversed by the Touhy needle, the solid stylet is removed from within the hollow needle, and an air filled syringe is coupled to the proximal luer fitting of the hollow needle. With pressure being applied to the plunger of the syringe as well as to the barrel of the syringe, the hollow needle of the Touhy needle is slowly advanced past the interspinous ligament and ligamentum flavum until the needle enters the epidural space between the ligamentum flavum and the dura mater of the spine. Location of the epidural space which is filled with connective tissue, fatty tissue, and blood vessels is indicated by loss of resistance; i.e., less resistance to the injection of air through the needle. In other words, when the pressure applied by the practitioner to the plunger causes the plunger to readily push air through the needle, the practitioner can assume that the epidural space has been reached. Upon entry to the epidural space, the syringe is carefully disconnected from the hollow needle (extreme care being taken to keep the needle in its exact position), and a catheter is threaded through the hollow needle. Because the hollow needle has an angled distal end, upon reaching the distal end of the hollow needle, the catheter is directed into the epidural space which is substantially perpendicular to the direction of the needle. The catheter is advanced only two to three centimeters into the epidural space in order to reduce the likelihood that it might exist though an intervertebral foramen, with resulting inadequate epidural anesthesia. With the catheter in place, a test dose, repeated injections, or a continuous flow of anesthesia may be administered through the catheter.

While the apparatus and methods for administering epidural anesthesia have proved successful over a long period of time, there are several drawbacks to the presently preferred techniques. First, it will be appreciated that even though the Touhy needle is provided with a curved Huber point, the Touhy needle is still sharp. Use of the Touhy needle therefore runs the risk that the practitioner might overshoot the epidural space and enter the subdural space between the dura mater and the arachnoid mater of the spine, or the subarachnoid space between the arachnoid mater and pia mater of the spine. Such a mistake could result in extreme over-application of anesthesia with a possible irreversible paralysis resulting. Similar complications could also occur during the disconnection of the syringe from the Touhy needle and insertion of the catheter, as the patient might move, or the needle might not be held properly in position. Such movement of the needle could result in the undesirable entry of the needle and/or catheter into the subdural or subarachnoid spaces.

SUMMARY OF THE INVENTION

It is therefore an object of the invention to provide a catheter-introducing needle assembly which presents a blunt distal end.

It is another object of the invention to provide a blunt ended catheter-introducing needle assembly which provides an indication when the tip of the needle assembly has reached a structural wall.

It is a further object of the invention to provide a blunt ended needle assembly through which a catheter can be introduced.

It is an additional object of the invention to provide a blunt ended needle assembly which can introduce a catheter into a space which is substantially perpendicular to the direction of insertion of needle assembly.

Another object of the invention is to provide a needle assembly and methods of using the needle assembly which are particularly useful in epidural anesthesia.

A further object of the invention is to provide a needle assembly which is useful in epidural anesthesia and which substantially reduces risks associated with the introduction of an epidural catheter.

In accord with these objects which will be discussed in detail below, the needle assembly of the present invention includes a hollow cannula having a sharp distal end, a hollow stylet having a blunt distal end with a radial opening and an interior deflection surface near the radial opening, and means for biasing the stylet in a first position where the blunt distal end of the stylet extends beyond the sharp distal end of the cannula. Preferably, the hollow cannula has a proximal end which is coupled, e.g., via insert molding, to a hollow cannula hub. Likewise, the stylet preferably includes a proximal end which is coupled, preferably via insert molding, to a hollow stylet hub which is longitudinally movable within the hollow cannula hub. The means for biasing typically comprises a spring inside the cannula hub which biases the stylet hub to the first position where the blunt distal end of the stylet extends beyond the sharp distal end of the cannula. The stylet is movable against the spring to a second position so that the blunt distal end of the stylet is depressed and the sharp distal end of the cannula is presented as it extends beyond the blunt distal end of the stylet. A first indicator is provided on the cannula hub showing the position of the stylet relative to the cannula, and a cannula orientation indicator on the cannula shows the direction of the radial opening. With the provided apparatus, in moving through the skin and ligaments, etc., the sharp needle is presented due to the stylet being depressed against the spring. However, upon entering the epidural space, the blunt ended stylet will spring forward and prevent the needle from presenting itself against the dura mater.

Preferred aspects of the invention include providing a key and keyway engagement between the hollow cannula hub and the hollow stylet hub so that the stylet is prevented from rotation relative to the cannula and the cannula hub. The first indicator is preferably created by providing a red and green indicator ring on the proximal end of the cannula and providing an opaque sleeve with a window on the stylet hub. The opaque sleeve is arranged to be movable over the indicator rings so that the window overlies the green indicator ring when the stylet is in the first position and overlies the red indicator ring when the stylet is depressed or retracted and the sharp distal end of the cannula is presented.

Additional objects and advantages of the invention will become apparent to those skilled in the art upon reference to the detailed description taken in conjunction with the provided figures.

BRIEF DESCRIPTION OF THE DRAWINGS

FIG. 5 is a side elevation view of the flanged cylindrical member with keyway;

FIG. 5a is a cross sectional view along line A—A in FIG. 5;

FIG. 6 is an enlarged broken longitudinal cross sectional view of an alternate embodiment of the stylet;

FIG. 7 is an enlarged broken longitudinal cross sectional view of a second alternate embodiment of the stylet;

FIG. 8 is an enlarged broken top view of a third alternate embodiment of the stylet;

FIG. 8a is an enlarged broken longitudinal cross sectional view of the stylet of FIG. 8;

DETAILED DESCRIPTION OF THE PREFERRED EMBODIMENTS

Figure 1:
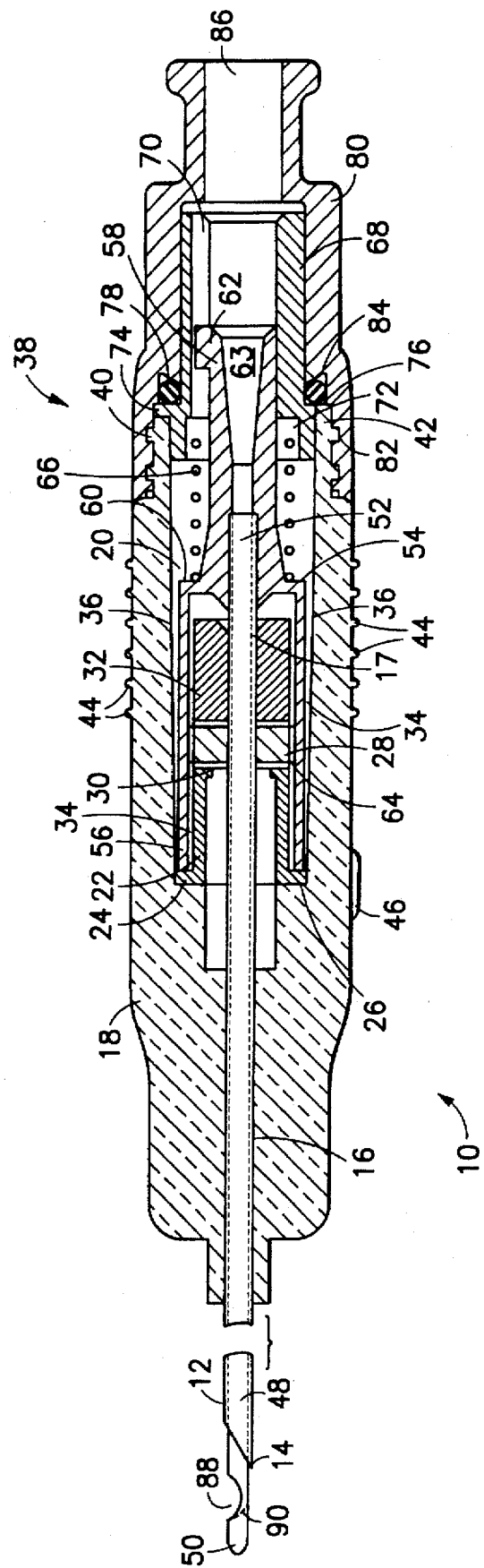
FIG. 1 is a broken longitudinal cross sectional view of the fully assembled needle assembly of the invention.
Figure 2:
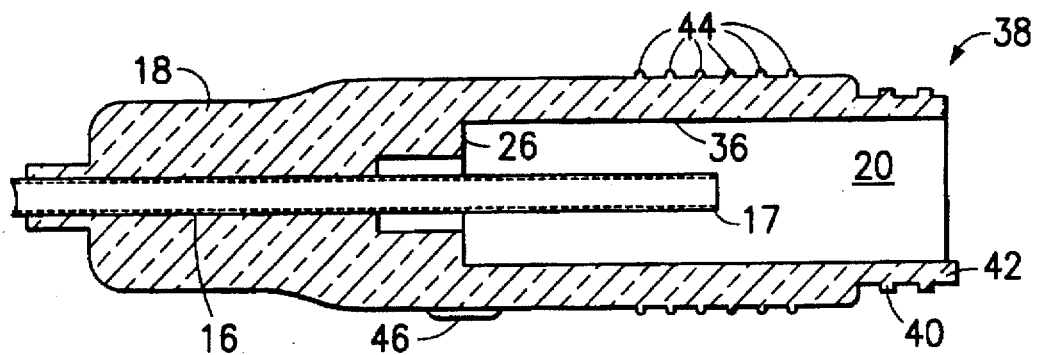
FIG. 2 is a broken longitudinal cross sectional view of the cannula and cannula hub prior to assembly.
Figure 3:
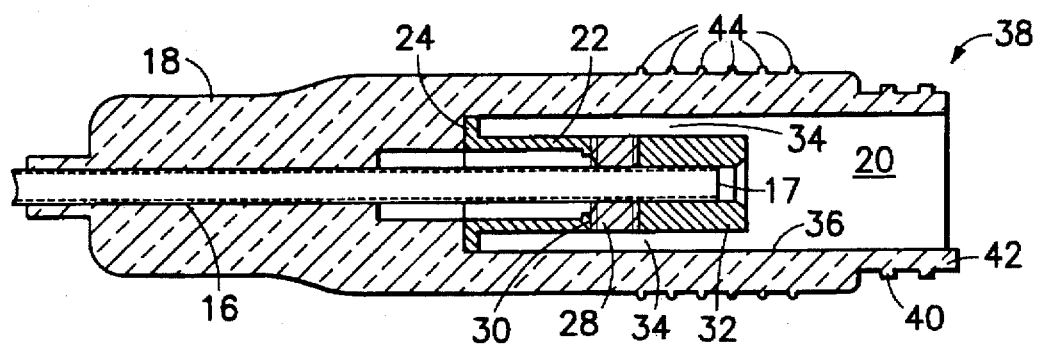
FIG. 3 is a view similar to FIG. 2 but in a stage of partial assembly.

Turning now to FIGS. 1 through 4 and 4a, the needle assembly 10 according to the invention includes a hollow cannula 12 having a sharpened distal end 14 and a proximal portion 16 which is preferably insert molded in a transparent hollow cannula hub 18. The proximal end 17 of the cannula extends approximately half way into the hollow interior 20 of the cannula hub 18. A cylindrical spacer 22 having a distal annular flange 24 is inserted over the proximal end 17 of the cannula 12 until the distal flange 24 abuts the distal annular base 26 of the hollow interior 20 of the cannula hub 18. A first indicator ring 28 having a first pigmentation, preferably green, representing a safety condition, is press fit over the proximal end 17 of the cannula 12 to abut the proximal end 30 of the cylindrical spacer 22 and hold the cylindrical spacer 22 against the distal end 26 of the hollow interior 20 of the cannula hub 18. A second indicator ring 32 having a second pigmentation, preferably pink or red, indicating an unsafe condition is press fit over the proximal end 17 of the cannula 12 and abuts the first indicator ring 28. The spacer 22 and the indicator rings 28, 32 have substantially the same outer diameter and align to form an annular space 34 between them and the interior wall 36 of the hollow cannula hub 18. The proximal end 38 of the cannula base 18 has exterior threads 40 and a lower proximally extending key portion 42. The outer surface of the cannula hub 18 is preferably provided with a ridged finger gripping surface 44 and an indicator marking 46 for indicating the angular position of the cannula hub 18 relative to the longitudinal axis of the cannula 12.

Figures 4, 4A:
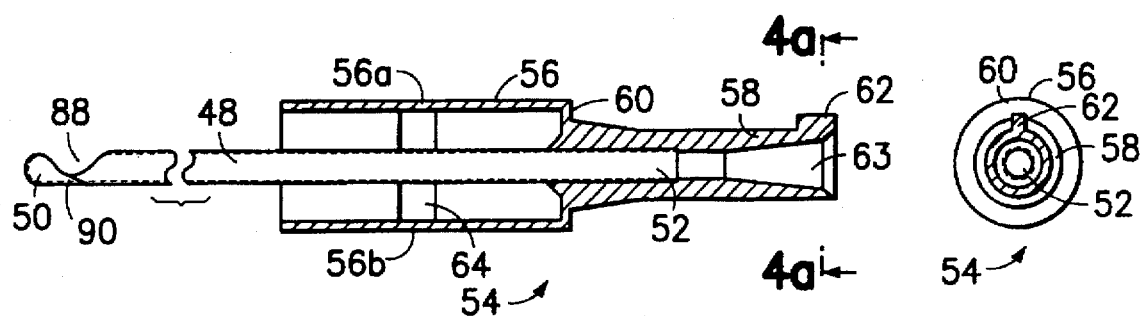
FIG. 4 is a broken longitudinal cross sectional view of the stylet and stylet hub prior to assembly.
FIG. 4a is a cross sectional view along the line A—A in FIG. 4.

A hollow stylet 48 has a blunt distal end 50 and a proximal end 52 which is insert molded in a hollow stylet hub 54. The stylet 48 extends through the cannula 12 so that the blunt distal end 50 of the stylet 48 extends beyond the sharpened distal end 14 of the cannula 12. The stylet hub 54 has a stepped profile with a wide distal sleeve portion 56 and narrower proximal keyed portion 58 defining an exterior spring seat 60 therebetween. The proximal keyed portion 58 of the stylet hub 54 has a tab key 62 extending radially outward therefrom and an interior fluid and catheter throughbore 63 in fluid communication with the interior of the stylet 48. The distal sleeve portion 56 of the stylet hub 54 is dimensioned to fit in the annular space 34 formed by the cylindrical spacer 22 and indicator rings 28, 32 in the hollow interior 20 of the cannula hub 18. The sleeve portion 56 is substantially opaque except for a transparent window portion 64. The window portion 64 may be simply formed by molding, or by cutting away side walls of the sleeve portion 56 while maintaining at least two webs 56a, 56b in the side wall as shown in FIG. 4. A coil spring 66 is placed over the narrower proximal keyed portion 58 and abuts the external spring seat 60. A distally flanged cylindrical member 68 having a keyway 70 and an interior spring seat 72 is inserted into the proximal end 38 of the cannula hub 18 and engages the proximal end of the coil spring 66 with its interior spring seat 72. The distal flange 74 of the cylindrical member 68 is provided with a notch 76 (seen best in FIG. 5a described below) which engages the key portion 42 of the cannula hub 18 and locates the keyway 70 relative to the indicator marking 46 on the surface of the cannula hub 18. A sealing O-ring 78 is placed over the proximal end of the distally flanged cylindrical member 68 and abuts its distal flange 74. A hollow screw cap 80 having distal interior threads 82, an interior seat 84 and a proximal luer coupling 86 is screwed onto the proximal exterior threads 40 of the cannula hub 18 and engages the proximal side of the O-ring 78 and presses it against the distal flange 74 of the distally flanged cylinder 68. The luer coupling 86 permits a syringe to be coupled to the proximal end of the needle assembly so that a loss of resistance technique can be utilized.

From the foregoing, it will be appreciated that the stylet 48 is biased in the distal direction so that its blunt distal end 50 is biased to a position distal of the sharp distal end 14 of the cannula 12 and that the stylet 48 is movable against the force of the coil spring 66 in the proximal direction. The dimensions of the parts described above are such that when the stylet 48 is moved in the proximal direction against the force of the coil spring 66, the sharp distal end 14 of the cannula 12 is exposed so that the cannula may puncture dense tissue. It will also be appreciated that when the stylet 48 is in the position where it extends beyond the distal end 14 of the cannula 12, the window portion 64 of the stylet hub 54 overlies the first indicator ring 28 and that when the stylet 48 is in the position where it exposes the distal end 14 of the cannula 12, the window portion 64 of the stylet hub 54 overlies the second indicator ring 32. It will further be appreciated that a fluid and catheter path is established between the proximal luer coupling 86 and the hollow interior of the stylet 48 through the through bore 63 in the stylet hub 54. The fluid and catheter path permits the needle assembly to be used in conjunction with a syringe without requiring removal of parts, and also permits a catheter to be inserted therethrough.

According to the invention, the distal end of the stylet 48 is provided with a radial opening 88 and an interior deflection surface 90 in the vicinity of the radial opening 88. The purpose of the deflecting surface 90 and the radial opening 88 is so that a catheter which is inserted into the luer coupling will travel freely through the hollow stylet to the deflection surface and be deflected to exit through the radial opening in the distal end of the stylet at an angle relative to the longitudinal axis of the stylet as shown and described in more detail below with reference to FIG. 10b. The radial opening 88 is positioned on the surface of the stylet relative to the key 62 on the stylet hub 54 so that the position of the key 62 indicates the direction of the radial opening 88. Moreover, as mentioned above, the position indicator 46 is located on the cannula hub 18 relative to the cannula hub key 42 which engages the cylindrical member 68 which carries the stylet hub keyway 70. From the foregoing, those skilled in the art will appreciate that the indicator marking 46 on the cannula hub 18 provides an indication of which direction the radial opening 88 in the stylet is facing and thus which direction a catheter will be deflected when a catheter is inserted through the stylet.

Turning now to FIGS. 6 through 8 and 8a, there are several different ways the interior deflection surface may be formed. As shown in FIG. 6, the distal end of the stylet 48 may be filled with a material 190 which will solidify and stick to the interior of the stylet 48. Such materials may include epoxy, solder, or the like. The material is preferably applied so that it solidifies with an inclined proximal surface 192. After the material solidifies, a side portion 188 of the stylet is ground away to form both the radial opening 88 and the deflecting surface 90. Alternatively, the radial opening 88 could be formed prior to introduction of the solidifying material.

Another way of forming the deflecting surface is shown in FIG. 7. Here, a radial indentation 290 is made in the wall of the stylet approximately 180 degrees apart from the radial opening 88 to create a deflecting surface 90. Preferably, the indentation is made just proximal the radial opening.

Yet a third way of forming the deflecting surface and the radial opening is shown in FIGS. 8 and 8a. Here, a semicircular or semi-elliptical cut 390 is made in the surface of the stylet 48 as shown in FIG. 8 to create a tongue which is depressed into the interior of the stylus as shown in FIG. 8a. The outer surface of the tongue becomes the deflecting surface 90 and the opening from which the tongue was cut becomes the radial opening 88. As mentioned above, the needle assembly of the invention is useful for installing catheters in a narrow space such as the epidural space which lies beneath the ligamentum flavum and above the dura mater. When administering epidural anesthesia, it is critical that the anesthesia catheter be placed properly in the epidural space. FIGS. 9, 9a, 10, 10a, and 10b show schematically how the invention is advantageously used to install an epidural catheter.

Figure 9:
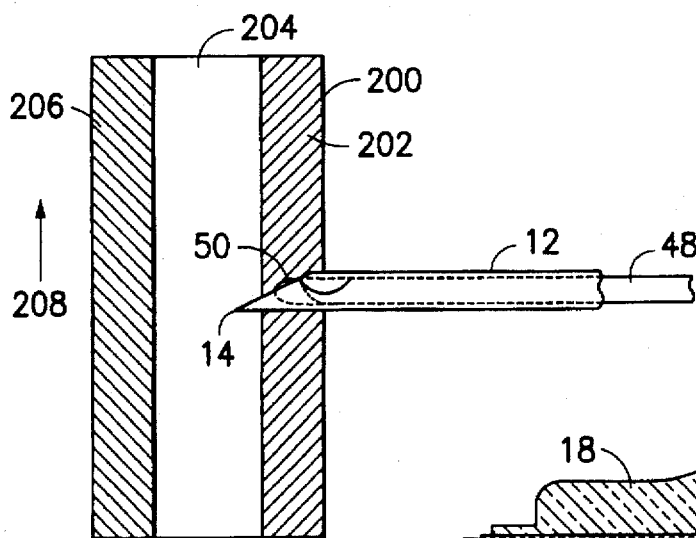
FIG. 9 is a broken longitudinal cross sectional view of the distal end of the needle assembly during a first stage of insertion into a schematic representation of the epidural space.
Figure 9A:
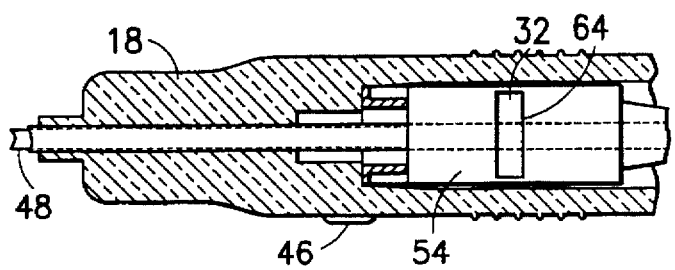
FIG. 9a is a broken longitudinal cross sectional view of the proximal end of the needle assembly in during the first stage of insertion showing the position of the stylet hub window relative to the indicator rings.
Figure 10:
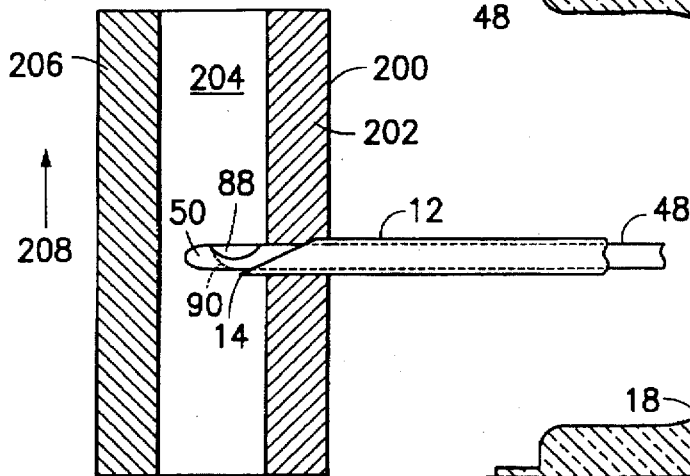
FIG. 10 is a view similar to FIG. 9 but showing the needle assembly in the second stage of insertion with the distal end of the stylet in the epidural space.
Figure 10A:
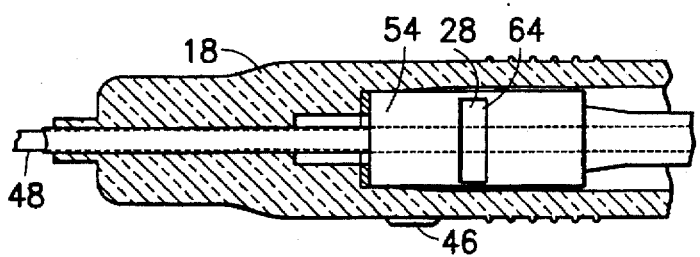
FIG. 10a is a view similar to FIG. 9a but showing the position of the stylet hub window relative to the indicator rings when the needle is in the second stage of insertion.
Figure 10B:
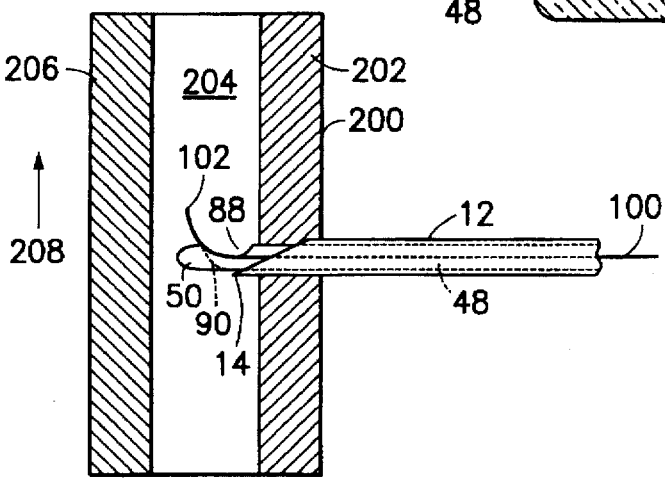
FIG. 10b is a view similar to FIG. 10 showing the insertion of a catheter through the stylet.

FIGS. 9, 10, and 10b show schematic views of the epidural space 204 which is bounded on one side by the ligamentum flavum 202 which lies beneath the epidermis and other tissues 200 and on the other side by the dura mater 206. The epidural space 204 extends narrowly along the axis 208 of the spinal canal (not shown). When the needle of the invention is inserted into the epidermis 200, the stylet 48 is pushed proximally against the coil spring 66 (FIG. 1) and the sharp distal end 14 of the cannula 12 is exposed to pierce through tissue. In this position, which is shown schematically in FIG. 9, the opaque stylet hub 54 is pushed back in the cannula hub 18 so that the clear window 64 in the stylet hub exposes the second (pink) indicator ring 32, thereby indicating that the sharp distal end 14 of the cannula 12 is exposed as shown in FIG. 9a. As the needle assembly is advanced through the ligamentum flavum 202, the stylet is kept pressed in the proximal position until the sharp distal end 14 enters the epidural space 204. It will be appreciated that the blunt end 50 of the stylet 48 blocks the hollow interior of the cannula 12 so that it does not become clogged tissue. Similarly, the radial opening 88 in the stylet 48 is covered by the cannula 12 and is not clogged with tissue. When the sharp distal end 14 enters the epidural space 204, the stylet is biased by the coil spring into the space 204 as shown in FIG. 10. Simultaneously, the styler hub 54 moves distally to the position shown in FIG. 10a where the window 64 in the stylet hub 54 exposes the first (green) indicator ring 28. The green indicator now indicates that the radial opening 88 in the stylet 48 lies within the epidural space 48. Further advancement of the needle assembly toward the dura mater 206 is possible, but when the blunt tip 50 of the stylet 48 reaches the dura mater, the stylet will be pushed proximally, and the indicator in the cannula hub will begin to show pink. Once the radial opening in the stylet is located in the epidural space, the direction of the opening is ascertained by noting the position of the indicator marking 46 on the cannula hub 18. The marking 46 may be aligned with the axis 208 of the spinal canal to choose the direction in which a cannula will be inserted. FIG. 10b shows how the distal end 102 of a hollow catheter 100 is deflected by the deflecting surface 90 to exit the stylet 48 through the radial opening 88.

There have been described and illustrated herein several embodiments of a needle assembly for use in installing a catheter in a direction which is at an angle to the needle assembly. While particular embodiments of the invention have been described, it is not intended that the invention be limited thereto, as it is intended that the invention be as broad in scope as the art will allow and that the specification be read likewise. Thus, while particular deflection surfaces and ways of creating them have been disclosed, it will be appreciated that other deflection surfaces could be utilized. For example, a laser cut-out may be made from the bottom opposite a radial opening, and bent upwards. Also, while a particular structure of the cannula hub assembly has been shown, it will be recognized that the structure of the cannula hub could be modified in several ways without departing from the spirit of the invention. Moreover, while particular configurations have been disclosed in reference to keys, keyways and indicators, it will be appreciated that other configurations could be used as well to determine the orientation of the radial opening in the stylet. Indeed, while the indicator rings were described as being green and pink or red, other colors such as yellow, and color combinations, e.g., yellow and red, etc., could be used. Furthermore, while the needle assembly has been described as useful in epidural anesthesia, it will be understood that the needle assembly is useful for installing a catheter in a narrow space where the catheter is directionally installed at an angle to the needle. It will therefore be appreciated by those skilled in the art that yet other modifications could be made to the provided invention without deviating from its spirit and scope as so claimed.

We claim:

1. A needle assembly for installing a catheter, comprising:
   a) a hollow cannula having a proximal end and a sharp distal end;
   b) a cannula hub coupled to said proximal end of said cannula;
   c) a hollow stylet extending through said hollow cannula, said hollow stylet having a proximal end, a blunt distal end, a radial opening near said blunt distal end, and an interior deflection surface near said radial opening such that a catheter inserted through said hollow stylet is deflected by said deflecting surface out through said radial opening;
   d) a stylet hub coupled to said proximal end of said stylet;
   e) biasing means coupled to said stylet hub and said cannula hub for biasing said stylet relative to said cannula to a first position where said blunt distal end of said stylet extends beyond said sharp distal end of said cannula, wherein said stylet is movable against said biasing means to a depressed second position where said sharp distal end of said cannula extends beyond said blunt distal end of said stylet; and
   f) indicator means on one of said cannula hub and said stylet hub for indicating a direction of said radial opening, said indicator means being rotationally fixed relative to said radial opening.

2. A needle assembly according to claim 1, comprising:
   g) position indicator on one of said cannula hub and said stylet hub for indicating when said stylet is in said first position.

3. A needle assembly according to claim 1, comprising:
   G) anti-rotation means on at least one of said cannula hub and said stylet hub for preventing axial rotation of said stylet relative to said cannula.

4. A needle assembly according to claim 1, wherein:
   said hollow stylet hub is contained within said hollow cannula hub and said hollow cannula hub is provided with a proximal fluid coupling in communication with said hollow stylet hub and the interior of said stylet.

5. A needle assembly for installing a catheter, comprising:
   a) a hollow cannula having a proximal end and a sharp distal end;
   b) a hollow stylet extending through said hollow cannula, said hollow stylet having a proximal end and a blunt distal end with a radial opening and an interior deflection surface near said radial opening;
   c) biasing means for biasing said hollow stylet in a first position where said blunt distal end of said stylet extends beyond said sharp distal end of said cannula, said stylet being movable against said biasing means to a second position where said sharp distal end of said hollow cannula extends past said blunt distal end of said stylet; and
   d) direction indicator means coupled to one of said proximal end of said cannula and said proximal end of said stylet for indicating the direction of said radial opening, said indicator means being rotationally fixed relative to said radial opening.

6. A needle assembly according to claim 5, further comprising:
   e) position indicator means coupled to one of said hollow cannula and said hollow stylet for indicating when said stylet is in said first position.

7. A needle assembly according to claim 5, further comprising:
   e) anti-rotation means coupled to one of said hollow stylet and said hollow cannula for preventing rotation of said stylet relative to said cannula.

8. A needle assembly according to claim 7, further comprising:
   f) position indicator means coupled to one of said hollow cannula and said hollow stylet for indicating when said stylet is in said first position.

9. A needle assembly according to claim 5, further comprising:
   e) a hollow cannula hub coupled to said proximal end of said cannula and having a proximal fluid port, said proximal fluid port being in fluid communication with said hollow cannula and said hollow stylet.

10. A needle assembly according to claim 9, further comprising:
    f) a hollow stylet hub coupled to said proximal end of said hollow stylet and movably mounted within said hollow cannula hub.

11. A needle assembly according to claim 10, wherein:
    said biasing means is coupled to said hollow stylet hub and said hollow cannula hub.

12. A needle assembly according to claim 11, wherein:
    said biasing means is a coil spring substantially coaxial with said hollow stylet.

13. A needle assembly according to claim 10, further comprising:
    g) anti-rotation means coupled to one of said hollow stylet hub and said hollow cannula hub for preventing rotation of one of said hollow stylet hub and said hollow cannula hub relative to the other.

14. A needle assembly according to claim 13, wherein:
    said anti-rotation means comprises a key on one of said hollow stylet hub and said hollow cannula hub and a keyway on the other of said hollow stylet hub and said hollow cannula hub.

15. A needle assembly according to claim 10, further comprising:
    g) a first pigmented member coupled to said cannula hub within said sleeve portion, wherein
    said hollow cannula hub is at least partially transparent,
    said hollow stylet hub includes a sleeve at least a portion of said sleeve being opaque and at least a portion of said sleeve being transparent, and
    when said stylet is in one of said first and second positions said first pigmented member is visible through said cannula hub and said transparent portion of said stylet hub and when said stylet is in the other of said first and second positions said first pigmented member is covered by said opaque portion of said sleeve.

16. A needle assembly according to claim 15, further comprising:

h) a second pigmented member coupled to said cannula hub within said sleeve portion, wherein when said stylet is in one of said first and second positions said first pigmented member is visible through said cannula hub and said transparent portion of said stylet hub and said second pigmented member is covered by said opaque portion of said sleeve, and when said stylet is in the other of said first and second positions said first pigmented member is covered by said opaque portion of said sleeve and said second pigmented member is visible through said cannula hub and said transparent portion of said stylet hub.

17. A method for installing a catheter through the epidermis into a body cavity, said method comprising:

a) providing a hollow cannula with a sharp distal end and a blunt tipped hollow stylet extending through the cannula;

b) biasing the stylet relative to the cannula in a first position where the blunt tip of the stylet extends beyond the sharp distal end of the cannula;

c) providing means for indicating when the stylet is in the first position;

d) pressing the blunt tip of the stylet against the epidermis until the stylet moves back through the cannula exposing the sharp distal end of the cannula;

e) piercing the epidermis with the sharp distal end of the cannula;

f) advancing the distal end of the cannula toward the body cavity;

g) noting when the means for indicating indicate that the stylet is in the first position; and h) threading the catheter through the stylet into the body cavity.

* * * * *